United States Patent [19]

Rigg et al.

[11] Patent Number: 5,622,692
[45] Date of Patent: Apr. 22, 1997

[54] METHOD AND APPARATUS FOR CUSTOMIZING FACIAL FOUNDATION PRODUCTS

[75] Inventors: Richard T. Rigg, Springfield Gardens, N.Y.; John R. Castro, Stamford; Pamela A. Petro, Shelton, both of Conn.; John A. Szweda, River Vale, N.J.

[73] Assignee: Elizabeth Arden Company, Division of Conopco, Inc., New York, N.Y.

[21] Appl. No.: 416,585

[22] Filed: Apr. 3, 1995

Related U.S. Application Data

[62] Division of Ser. No. 110,274, Aug. 23, 1993.

[51] Int. Cl.$^6$ ................................................. A61K 7/021
[52] U.S. Cl. ................ 424/63; 364/400; 364/479.02; 364/479.09; 366/160.1; 366/162.1
[58] Field of Search .................. 424/63; 364/400, 364/479; 366/160, 162

[56] References Cited

U.S. PATENT DOCUMENTS

| | | |
|---|---|---|
| 4,090,632 | 5/1978 | McFarlane . |
| 4,160,271 | 7/1979 | Grayson et al. . |
| 4,272,824 | 6/1981 | Lewinger et al. . |
| 4,705,083 | 11/1987 | Rossetti . |
| 4,871,262 | 10/1989 | Krauss et al. ............... 366/160 |
| 4,911,544 | 3/1990 | Walsh . |
| 4,967,938 | 11/1990 | Hellenberg . |
| 4,977,522 | 12/1990 | David . |
| 5,003,500 | 3/1991 | Gerber . |
| 5,078,302 | 1/1992 | Hellenberg . |
| 5,163,010 | 11/1992 | Klein et al. ............... 364/479 |

FOREIGN PATENT DOCUMENTS

| | | |
|---|---|---|
| 0319375 | 6/1989 | European Pat. Off. . |
| 0443741 | 8/1991 | European Pat. Off. . |
| 0484564 | 5/1992 | European Pat. Off. . |
| 2380151 | 2/1978 | France . |
| 2669526 | 5/1992 | France . |
| 4110299 | 3/1991 | Germany . |
| 1589705 | 5/1981 | United Kingdom . |
| 2071573 | 9/1981 | United Kingdom . |
| WO93/24074 | 12/1993 | WIPO . |

OTHER PUBLICATIONS

International Search Report.
Article Entitled "Anti-Wrinkle Revolution", Self Magazine, Nov. 1992, p. 132.
Advertisement for Clinique appearing in the New York Times Magazine, Oct. 25, 1992. p. 21.

*Primary Examiner*—Shelley A. Dodson
*Attorney, Agent, or Firm*—Milton L. Honig

[57] ABSTRACT

A method and apparatus is provided for customizing a facial foundation product at point of sale to a customer. Three essential elements are that of a skin analyzer for reading skin properties, a programmable device receiving the reading and correlating same with an optimal formula from a preprogrammed set of formulas, and a formulation machine for preparing the facial foundation product from various cosmetic chemical compositions. The formulation machine receives instructions from the programmable device on the optimal formula. This formula is then dosed and blended from a series of dispensers containing separate cosmetic chemical compositions into a receiving bottle. The optimal formula may be altered through customer preferences by manual alteration of the selected optimal formula.

13 Claims, 1 Drawing Sheet

METHOD AND APPARATUS FOR CUSTOMIZING FACIAL FOUNDATION PRODUCTS

This is a Divisional of Ser. No. 08/110,274 filed Aug. 23, 1993.

BACKGROUND OF THE INVENTION

1. Field of the Invention

The invention concerns a method and apparatus for customizing a facial foundation product at the point of sale to a customer.

2. The Related Art

Selection of the optimal color shade is often a customer's chief concern in purchasing a cosmetic facial product. A number of companies in the industry have sought to render easier the selection process. Clinique and Clarion have installed computers at sales counters for use by the customer. Information on color shade, oiliness and other properties of a customer's skin are punched into the computer which then determines the company's most closely matching product.

Another point of sale technique has been that of custom blending. Two major companies, Prescriptives (division of Estee Lauder) and Visage (division of Revlon) begin a sale by manually evaluating a subject's skin color. The salesperson then adjusts existing finished foundations so as to match the evaluated skin color. Unfortunately, there are many disadvantages in manual blending. The most obvious of these is that too much time is required for a match, sometimes 30–45 minutes. On many occasions there is a poor skin match, reproducibility is poor and extensive training is required of the salesperson.

Within the patent literature, U.S. Pat. No. 4,871,262 (Krauss et al) describes an automatic cosmetic dispensing system for blending selected additives into a cosmetic base. The system is intended for use at a retail establishment. A similar system is described in German Patent 41 10 299 C1 (Erdtmann), with the further element of a facial sensor. Although the aforementioned systems have advanced the art, additional refinements have become necessary to achieve commercial acceptability in terms of speed and accuracy of product delivery.

Accordingly it is an object of the present invention to provide a method and apparatus that will reduce time-required for matching skin properties with a particular optimum formula.

Another object of the present invention is to provide a method and apparatus for matching skin properties with an optimal cosmetic formula in a manner that is both accurate and repeatable.

A further object of the present invention is to provide a method and apparatus for matching skin properties with an optimal cosmetic formula that requires only minimal training for the salesperson in selecting the proper product.

A still further object of the present invention is to provide a method and apparatus for matching skin properties with an optimal cosmetic formula and then rapidly and highly accurately dispensing the chosen cosmetic product.

These and other objects of the present invention will become more readily apparent through consideration of the following summary, drawing and detailed description which follow.

SUMMARY OF THE INVENTION

A method for customizing a facial foundation product at point of sale to a customer is provided wherein the method includes:

(i) obtaining a reading of a customer's natural skin coloration by applying a device for measuring coloration in proximity to the skin;

(ii) transmitting the reading to a programmable device for selecting an optimal facial foundation formula by correlating the reading with one of a preprogrammed set of formulas;

(iii) transferring the selected preprogrammed formula as operating instructions to a formulation machine for automatically preparing the formula;

(iv) dosing together within the formulation machine a plurality of cosmetic chemical compositions including at least one pigment, the plurality of compositions being chosen in accordance with information provided by the selected preprogrammed formula; and (v) delivering into a container the dosed formula to the customer as a facial foundation product.

An apparatus for customizing a facial foundation product at point of sale to a customer is also described herein, the apparatus including:

(i) a device for measuring a customer's natural skin coloration and for generating a signal conveying information on the measured natural skin coloration;

(ii) a programmable device for receiving the signal, for correlating the signal with one of a preprogrammed set of formulas, and for selecting an optimal formula from the preprogrammed set; and (iii) a formulation machine for preparing the facial foundation product including:
  (a) a mechanism for receiving the optimal formula as a set of operating instructions;
  (b) a plurality of dispensers each containing a different cosmetic chemical composition including at least one pigment;
  (c) a mechanism for activating dosing to a common dosing chamber of certain of the cosmetic chemical compositions and at certain concentrations as determined by the operating instructions; and
  (d) a mechanism for delivering the dosed formula into a container to the customer as a facial foundation product.

Besides natural skin coloration, a variety of skin characteristics may be measured including moisturization, oiliness, texture and irritation sensitivity. The measuring device may be a spectrophotomer. One or more light-emitting diodes may form the sensor portion of the spectrophotomer. Both visible and infrared wavelength light may be utilized in connection with the light-emitting diodes.

Advantageously, at least some of the cosmetic chemical compositions will be monochromatic emulsions. Most preferred is that the formulation machine contain at least four dispensers separately containing a red, yellow, black and white monochromatic composition. Either in separate dispensers or as ingredients of the monochromatic emulsions there may be included emollients, sunscreens, moisturizers, perfumes, solvents and wrinkling and skin-aging inhibitors.

An identification mark may be assigned to each customized facial foundation product. The marking may be labeled on the container as well as stored within the programmable device and permanently identified with the customer. Especially useful as the marking is a bar code.

BRIEF DESCRIPTION OF THE DRAWING

Features and advantages of the present invention will more fully be appreciated by reference to the FIGURE which is the sole drawing and which diagrammatically illustrates the customization system.

DETAILED DESCRIPTION

Figure 1:
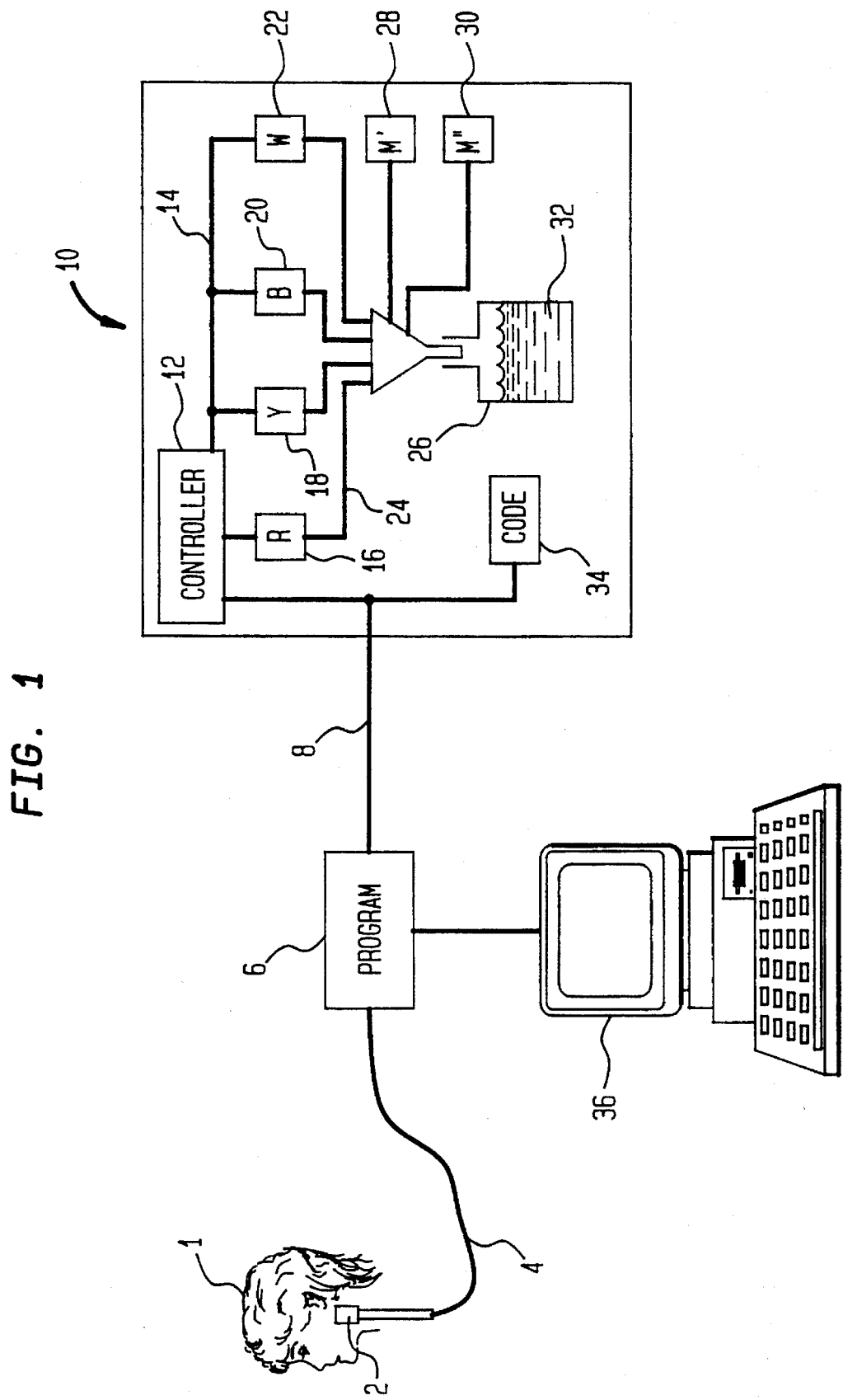

In accordance with the invention, the system has three essential modules. These modules include an electronic skin analyzer, a computer with preprogrammed formulas and a machine for dispensing-mixing of the cosmetic chemical compositions. These modules will be capable of electronically communicating with one another.

The skin analyzing module is preferably a hand-held spectrophotometer operating with at least one, but preferably four or more light-emitting diodes (LED). Suitable skin analyzers are commercially available from Minolta Camera Co. Ltd, Japan (Minolta Spectrophotometer CM-2002) and from Colortec Associates (diffused illumination/diffused viewing) Spectrophometer.

The second essential component of the apparatus is that of a programmable device which may be a module separate from or housed commonly within the skin analyzing unit. The programmable device will include a preprogrammed menu of at least 25, preferably several hundred, optimally several thousand facial foundation formulas directed at a particular facial foundation product.

A third essential module of the apparatus is that of a formulation machine. The machine will include a series of dispensers, each containing a different cosmetic chemical composition. Each of the dispensers will be connected into a common dosing chamber through respective tubing. An electronic control board will also be part of the machine. This board will receive electronic instructions from the programmable device as to the optimal formula necessary to be dispensed. Servomechanical activators will be present within the machine to operate discharge valves for the respective dispensers. In accordance with the selected optimal formula, the requisite valves will be opened and the length of opening time will be regulated pursuant to the required quantity of any particular cosmetic chemical composition to be dispensed. Advantageously, the dosing chamber will be in the form of a disposable dispensing container provided directly to the customer and serving as the packaged bottle. The machine will also be capable of adjusting sample sizes of the dosed-mixed optimal formula.

A marking mechanism may also be associated with the apparatus, preferably housed together with the formulation machine. The marking mechanism may utilize any numerical scheme, e.g. a customer's name, Social Security number, and/or other personalized identification, for connection with the optimal cosmetic product selected through the skin measuring process. Advantageously, the marking will be in the form of a bar code symbol.

Sometimes a customer may wish to alter the preprogrammed optimal formula. For such purpose, a further module is provided wherein a customers preference can be entered to the program through a keyboard.

A highly diagrammatic representation of the apparatus is provided in the FIGURE. Therein is shown a customer 1 whose facial skin is being measured by a skin analyzer 2. The resultant reading or signal is transferred electronically via line 4 into a programmable device 6. A preprogrammed set of formulas is reviewed for correlation with the skin reading. The optimal formula is then identified and that information is transferred via line 8 to a formulation machine 10 where it is directed to a controller unit 12. Servomechanical devices 14 are operated in conjunction with the information on the optimal formula.

When a particular facial foundation is required, an optimal color shade is delivered by combining a mixture of monochromatic compositions each of which is dosed from a respective dispenser. These dispensers contain a cosmetic chemical composition exhibiting one of four monochromatic colors, i.e. Red 16, Yellow 18, Black 20 and White 22. These colors will typically be achieved by incorporation of a respective iron oxide pigment (e.g. red iron oxide, yellow iron oxide or black iron oxide). White can be obtained from titanium dioxide.

The servomechanical device 14 operates a series of valves associated with each of the dispensers to deliver the proper amount of each monochromatic colored composition. Delivery is through a system of tubing 24 which leads to a common dosing chamber 26. The dosing chamber is shown as an empty cosmetic bottle ready for sale to the customer. A moisturizing composition M' or modifying finish M" may also be provided from separate dispensers 28, 30 into the dosing chamber 26. The customized facial foundation product 32 is then inspected by the customer. Any customer changes may be inputted to programmable device 6 for alteration of the preprogrammed optimum formula by instructions manually transmitted into the keyboard terminal 36. A second, final facial foundation product is then dispensed, mixed and bottled. Affixed to the bottle 32 will be a bar code printed through coder 34.

The method for customizing the cosmetic product is as follows. A region on a customer's face will be cleaned preparatory to a reading. The LED device will then be placed in proximity to the cleaned facial area. Visible light emitted by the LED will be reflected off the skin surface and the altered wavelength measured. A total of three skin readings along the neck/jaw line region will be taken. Total time for the reading will be approximately 30 seconds.

The collected wavelength information will then be transmitted to the programmable device. The program of the device will correlate the LED reading with a preprogrammed optimal formula. Information on this formula will then be transferred to the controller portion of a formulation machine. This information will then be translated into operating instructions to the dispensing unit. The selected cosmetic chemical compositions and their amounts will then be dosed to a dispensing container. The initial run will generate a trial sample of 5–10 ml which is given to the customer for review. Any necessary change in the formula, e.g. the color shade change, will then be manually programmed through a keyboard terminal into the programmable device. Again, instructions will be sent to the controller of the formulation machine and an adjusted sample will be dispensed-mixed and dosed in a full-size sample to an empty container bottle. A bar code containing shade and formula information is then affixed to the sample. Information on the purchased cosmetic formula will also be stored in a central computer. At any subsequent time, the customer can return to this or any other store having access to the system. Based on the bar code information, the exact same optimal formula can be prepared as a refill.

The method of this invention allows preparation of a relatively infinite number of different cosmetic formulations, e.g. color shades, to allow for enormous variations. These products are also freshly manufactured at the point of sale thereby avoiding any settling or decomposition during storage. Most significantly, there will be no necessity of maintaining in inventory a large number of different shades of color cosmetic, many of which will never be sold. Moreover, the method promises that a specific color shade or formulation would not be discontinued for lack of sales. Availability of the customized formula will also be at any location where the system is installed.

The foregoing description illustrates selected embodiments of the present invention and in light thereof variations and modifications will be suggested to one skilled in the art, all of which are within the spirit and purview of this invention.

What is claimed is:

1. A method for customizing a facial foundation at point of sale to a customer comprising:
   (i) obtaining a reading of a customer's natural skin coloration by applying a means for measuring coloration in proximity to the skin;
   (ii) transmitting the reading to a programmable means for selecting an optimal facial foundation formula;
   (iii) transferring the selected optimal facial foundation formula as operating instructions to a formulation machine for automatically preparing the formula;
   (iv) dosing together within the formulation machine at least four cosmetic chemical compositions each of which are contained in a separate dispenser, the chemical compositions being respectively a red, yellow, black and white monochromatic composition, the plurality of compositions being chosen in accordance with information provided by the selected optimal facial foundation formula; and
   (v) delivering into a container the dosed formula to the customer as a facial foundation product.

2. A method according to claim 1 wherein the means for measuring coloration can also measure at least one skin characteristic selected from the group consisting of a customer's natural skin moisturization, oiliness, texture and irritation sensitivity.

3. A method according to claim 1 wherein the means for measuring is a spectrophotometer.

4. A method according to claim 3 wherein the spectrophotometer is formed with at least one light-emitting diode.

5. A method according to claim 3 wherein the spectrophotometer measures visible wavelength light which interacts with the skin.

6. A method according to claim 3 wherein the spectrophotometer measures infrared wavelength light which interacts with the skin.

7. A method according to claim 1 further comprising the step of a customer inputting a modification to alter the selected optimal formula.

8. A method according to claim 1 further comprising the step of assigning an identification mark to each customized facial foundation product, labeling on the container the mark, and storing the identification within the programmable means to permanently identify the customized facial foundation product with the customer.

9. A method according to claim 8 wherein the marking is in the form of a bar code.

10. A method for customizing a facial foundation at point of sale to a customer comprising:
    (i) obtaining a reading of a customer's natural skin coloration by applying a means for measuring coloration in proximity to the skin;
    (ii) transmitting the reading to a programmable means for selecting an optimal facial foundation formula;
    (iii) transferring the selected optimal facial foundation formula as operating instructions to a formulation machine for automatically preparing the formula;
    (iv) dosing together within the formulation machine a plurality of cosmetic chemical compositions including at least one pigment, the plurality of compositions being chosen in accordance with information provided by the selected optimal facial foundation formula;
    (v) delivering into a container the dosed formula to the customer as a facial foundation product; and
    (vi) assigning an identification mark to each customized facial foundation product, labelling on the container the mark, and storing the identification within the programmable means to permanently identify the customized facial foundation product with a customer.

11. A method according to claim 10 wherein there are at least four cosmetic chemical compositions, each of which are contained in a separate dispenser, and the compositions being respectively a red, yellow, black and white monochromatic composition.

12. A method according to claim 11 wherein the monochromatic compositions or other non-monochromatic cosmetic chemical compositions include ingredients that are selected from the group consisting of emollients, sunscreens, moisturizers, perfumes, solvents, and wrinkling and skin-aging inhibitors.

13. A method according to claim 10 wherein the marking is in the form of a bar code.

* * * * *